United States Patent [19]

Régnier et al.

[11] Patent Number: 4,479,952
[45] Date of Patent: Oct. 30, 1984

[54] MONOSUBSTITUTED PIPERAZINES

[75] Inventors: Gilbert Régnier, Chatenay Malabry; Jacques Buré, Neuilly-sur-Seine, both of France

[73] Assignee: Science Union Et Cie, Suresnes, France

[21] Appl. No.: 28,049

[22] Filed: Apr. 9, 1979

[30] Foreign Application Priority Data

Apr. 13, 1978 [GB] United Kingdom ............... 14565/78

[51] Int. Cl.³ .................. A61K 31/495; C07D 417/04
[52] U.S. Cl. .................................. 424/250; 544/367; 544/377; 544/390
[58] Field of Search .......................... 544/367; 424/250

[56] References Cited

U.S. PATENT DOCUMENTS 3,489,757 1/1970 Koppe et al. ................... 544/369
4,123,529 10/1978 Verge et al. .................... 544/369

Primary Examiner—Donald G. Daus
Assistant Examiner—James H. Turnipseed
Attorney, Agent, or Firm—Gordon W. Hueschen

[57] ABSTRACT

Monosubstituted piperazines of the formula:

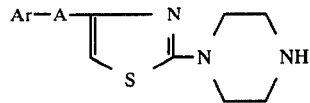

in which:
A is —(CH$_2$)$_n$—, n being 1, 2 or 3, or

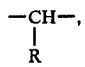

R being alkyl up to C$_5$ inclusive, trifluoromethyl, phenyl, halophenyl, lower-alkylphenyl, lower-alkoxyphenyl or trifluoromethylphenyl and
Ar is phenyl, halophenyl, lower-alkylphenyl, lower-alkoxyphenyl, methylenedioxyphenyl, hydroxyphenyl, or

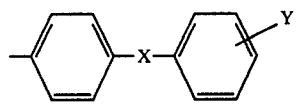

in which X is a single bond, oxygen, sulfur or carbonyl and Y is hydrogen, halogen, lower alkyl or lower alkoxy.

These compounds and their physiologically tolerable acid addition salts thereof may be used as medicines especially in the treatment of inflammation with immunological component.

6 Claims, No Drawings

MONOSUBSTITUTED PIPERAZINES

The present invention provides monosubstituted piperazines of the formula:

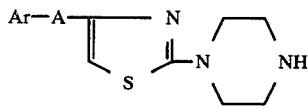   I in which:

A is selected from the group consisting of —(CH$_2$)$_n$—, in which n is selected from 1, 2 and 3, and

in which R is selected from the group consisting of alkyl radicals having from 1 to 5 carbon atoms inclusive, a trifluoromethyl radical, an unsubstituted phenyl radical and phenyl radicals mono- and polysubstituted by a substituent selected from the group consisting of halogen atoms, alkyl and alkoxy radicals each having from 1 to 5 carbon atoms inclusive and a trifluoromethyl radical, and Ar is selected from the group consisting of:

an unsubstituted phenyl radical and phenyl radicals mono- and polysubstituted by a substituent selected from the group consisting of halogen atoms, alkyl and alkoxy radicals each having from 1 to 5 carbon atoms inclusive, methylenedioxy, hydroxy and trifluoromethyl radicals, and a radical of the formula

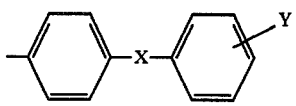

wherein:

X is selected from the group consisting of a single bond, an oxygen atom, a sulfur atom and a carbonyl radical, and Y is selected from the group consisting of a hydrogen atom, halogen atoms and alkyl and alkoxy radicals each having from 1 to 5 carbon atom inclusive.

In the here-above definitions, there may be mentioned for example as halogen atoms: chlorine, bromine, and fluorine atoms, as alkyl radicals: methyl, ethyl, propylbutyl and pentyl radicals and as alkoxy radicals: methoxy, ethoxy, propoxy, butoxy and pentyloxy radicals.

The present invention also provides acid addition salts of the compounds of the general formula I. The acid addition salts are preferably physiologically tolerable acid addition salts.

The present invention further provides a process for preparing a compound of the general formula I which comprises condensing a halo compound of the general formula:

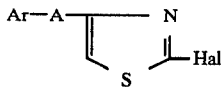   II in which Ar and A have the meanings given above and Hal represents a chlorine or a bromine atom, with an excess of piperazine.

Such a process is advantageously carried out by reacting the compound II with piperazine in solution in an aliphatic alcohol containing 4 or 5 carbon atoms, at a temperature within the range of from 110° to 140° C. The amount of piperazine may be from 2 to 5 times the stoicheiometric quantity, the excess acting as acceptor for the hydrogen halide formed during the reaction.

The present invention aldo provides as process for preparing a compound of the general formula I which comprises condensing a halo compound of the general formula:

   III in which Ar, A and Hal have the meanings given above, with a 1-substituted-4-thiocarbamoyl piperazine of the general formula

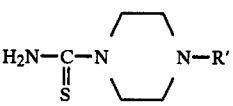   IV in which R' is a protecting group such for example as a formyl or an alkoxycarbonyl, preferable an ethoxycarbonyl radical, then hydrolysing the resulting compound of the general formula:

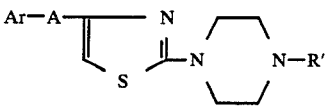   V in which Ar, A and R' have the meanings given above.

Such a process is advantageously carried out by reacting the compounds III and IV in solution in a polar solvent such for example as an aliphatic alcohol having from 2 to 4 carbon atoms, preferably at the boiling temperature of such a mixture, viz within the range of from 75° to 115° C., then hydrolysing the protecting group with a strong base such for example sodium or potassium hydroxide, in the same solvent.

The starting materials used for these processes are known compounds, or they may be prepared according to methods described in the literature for preparing similar compounds as mentioned in the following examples.

The compounds of the general formula I are strong bases which may be converted by treatment with acids into acid addition salts. As acids which may be used for the formation of these addition salts, there may be mentioned for example, in the mineral series: hydrochloric, hydrobromic, sulphuric and phosphoric acids; and in the organic series: acetic, propionic, maleic, fumaric, tartaric, citric, oxalic, benzoic, methanesulfonic and isethionic acids.

The compounds of the formula I may be purified by physical methods, for example, crystallization or chromatography, or by chemical methods, for example by formation of an addition salt followed by crystallization of the latter and decomposition thereof with an alkaline agent.

The compounds of the general formula I possess valuable pharmacological and therapeutic properties, especially anti-inflammatory properties, mainly when they are in connection with the starting of a secondary immunitary reaction.

They may, therefore, be used as medicines, especially in the fields in which there are some inflammatory symptoms dependent on an action of lymphocytes, maily in chronic inflammatory pathology with antoimune etiology (nephritis, thyroiditis etc . . . ) or with an antoimmune component comprising rheumatoid diseases, collagenosis, Crohn's disease etc . . . ; in chronic infectious pathology, caused by parasites, bacteria, virus and slow virus, with an inflammatory component in ORL, respiratory, urogenital, central nervous system or digestive tract areas (glomerulonephritis, endocarditis, pancreatitis with insulitis, hepatitis, chronic bronchitis, etc . . . ) as adjuvant to antiinfectious treatments or as independent treatment, and in some chronic and antiflammatory pathologies induced by other heteroantigens (transplant rejection, dermatitis by contact, and some chronic asthma, etc . . . )

Their toxicity is low and their $LD_{50}$ determined in mice per orally varies from 250 to more than 2500 mg/Kg according to the compounds.

The antiinflammatory activity was determined among others, by the test of Siegmund, E. A. and al. Proc. Soc. Exp. Biol. Med., (1957), 95, 729. When the compounds of the invention are administered to mice per orally at a dose of 50 mg/Kg there were observed inhibitions of the cramps provoked in the mice by the phenylbenzoquinone I.P. up to 93%.

The immunomodulating effect was studied according to the test of Asherson and al., Immunology (1968), 15, 405. When the compounds of the invention are administered to mice per orally at doses within the range of 25 to 100 mg/Kg, there were observed inhibitions of the inflammation in connection with cutaneous hypersensibility induced in mice by oxazolone which may reach 77%.

The present invention therefore provides pharmaceutical compositions containing as active ingredient a compound of the general formula I or a physiologically tolerable acid addition salt thereof, in admixture or conjunction with a pharmaceutically suitable carrier, such, for example, as distilled water, glucose, lactose, starch, talc, ethyl cellulose, magnesium stearate or cocoa butter.

The pharmaceutical composition of the present invention are advantageously in unit dosage form, and may contain from 20 to 200 mg of the active ingredient.

These pharmaceutical compositions may be in form of tablets, dragees, capsules, lipesomes for oral or injectable administration, suppositories, injectable or drinkable solutions, soluble preparations for intraarticular infiltrations, ointments, spray or aerosols, and may be administered by oral, rectal, parenteral or topical route at a dose of active ingredient within the range of 20 to 200 mg, one to four times a day.

The following examples illustrate the invention, the melting points being determined in a capillary tube, unless otherwise stated.

EXAMPLE I 1-(4-benzyl-2-thiazolyl) piperazine

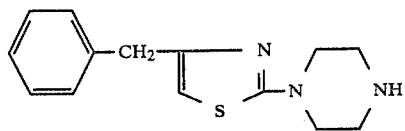

First method:

A solution of 14 g of 2-bromo-4-benzyl thiazole (B.P./3mmHg: 178°–180° C.) and 19 g of anhydrous piperazine in 200 ml of butanol was boiled for 5 hours. After the completion of the reaction, the piperazine hydrobromide which formed was filtered off and the solvent was evaporated under reduced pressure. The excess of anhydrous piperazine was eliminated by sublimation by heating of the syrupy residue at 100° C. under a reduced pressure of 1 mn of Hg. The residue, weighting 15 g, was treated with 200 ml of acetonitrile. The small residual amount of piperazine hydrobromide was filtered off and the solvent was evaporated under reduced pressure. The residue was dissolved in 100 ml of a normal solution of monomethanesulfonic acid and the solution was treatted with active charcoal. The filtrate was alkalized with an excess of potassium carbonate, the resulting base was extracted with two 50 ml portions of chloroform and the chloroform solution was dried over potassium carbonate. The solvent was then evaporated and there were obtained 13 g of beige crystals which after recrystallization from 30 ml of cyclohexane gave 7.5 g of 1-(4-benzyl-2-thiazolyl) piperazine in the form of white crystals melting at 73°–74° C.

The starting compound 2-bromo-4-benzyl thiazole was prepared by Sandmeyer reaction starting from 2-amino-4-benzyl thiazole itself prepared according to the method Mahajanshetti and Nargund J. Indian Chem. Soc. 39, 420 (1962), and all the other starting compounds of the formula II used in the following examples were prepared by the same method.

Second method:

A solution of 16.9 g of 1-phenyl-3-chloro acetone (B.P./0.15 mmHg=105°–106° C.) and 17.3 g of 1-formyl-4-thiocarbamoyl piperazine (oil) in 100 ml of ethanol was boiled for 6 hours. There were added to the solution 6 g of potassium hydroxid pellets and the mixture was heated to the boiling temperature for 15 hours in order to hydrolise the formyl protecting group. Then the solvent was evaporated off under reduced pressure and the residue was taken up with 100 ml of water and 150 ml of a normal solution of monomethanesulfonic acid. The insoluble matter was extracted with ether and the acid solution alkalized with an excess of potassium carbonate. The resulting base was extracted with chloroform then the solvent was evaporated. There were obtained 7 g of beige crystals which after recrystallization from cyclohexane gave 5 g of 1-(4-benzyl-2-thiazolyl) piperazine, as white crystals melting at 73°–74° C.

The starting compound 1-phenyl-3-chloro-acetone was prepared by reacting diazomethane with phenylacetyl chloride in tetrahydrofuran, according to the method of Mahajanshetti and Nargund, J. Indian Chem. Soc. 39, 420 (1962), and all the other starting compounds of the formula III used in the following examples were prepared by the same method.

The starting compound 1-formyl-4-thiocarbamoyl piperazine was prepared in analogy to the method described by Conroy and Denton J. Org. Chem. 18, 1489 (1953) starting from 4-formylpiperazine thiocyanate, M.P. 118° C.

EXAMPLE 2 TO 28

The following compounds were prepared in the manner described in the first method given in example 1, starting from an appropriate 2-bromo (or chloro)-4-substituted thiazole and an excess of piperazine, and in the manner described in the second method given in example 1, starting from an appropriate 1-substituted 3-chloro (or bromo) acetone and 1-formyl (or ethoxycarbonyl)-4-thiocarbamoyl piperazine.

(2) 1-[4-(4-biphenylylmethyl)-2-thiazolyl] piperazine, M.P. of its dihydrochloride hemihydrate: 215-220° C. (methanol/ether).

(3) 1-[4-(2-chlorobenzyl)-2-thiazolyl] piperazine, M.P. of its dihydrochloride hemihydrate: 175°-180° C. (anhydrous ethanol).

(4) 1-[4-(3-chlorobenzyl)-2-thiazolyl] piperazine, M.P. of its dihydrochloride hemihydrate: 160-168° C. (anhydrous ethanol).

(5) 1-[4-(4-chlorobenzyl)-2-thiazolyl] piperazine,, M.P. ot its dihydrochloride: 175°-180° C. (anhydrous ethanol).

(6) 1-[4-(2-methylbenzyl)-2-thiazolyl] piperazine.

(7) 1-[4-(3-methylbenzyl)-2-thiazolyl] piperazine, M.P. of its hemisulfate hemihydrate: 210°-215° C. (anhydrous ethanol).

(8) 1-[4-(4-methylbenzyl)-2-thiazolyl] piperazine, M.P. of its dihydrochloride hemihydrate: 65°-70° C., (anhydrous ethanol).

(9) 1-[4-(2-methoxybenzyl)-2-thiazolyl] piperazine

(10) 1-[4-(3-methoxybenzyl)-2-thiazolyl] piperazine.

(11) 1-[4-(4-methoxybenzyl)-2-thiazolyl] piperazine.

(12) 1-[4-(3,4-dimethoxybenzyl)-2-thiazolyl] piperazine.

(13) 1-[4-(3,4-methylenedioxybenzyl)-2-thiazolyl] piperazine.

(14) 1-[4-(3-trifluoromethylbenzyl)-2-thiazolyl] piperazine.

(15) 1-[4-(4-phenoxybenzyl)-2-thiazolyl] piperazine, M.P. of its hydrochloride: 236°-242° C. (anhydrous methanol/ether).

(16) 1-[4-(4-p.chlorophenoxybenzyl)-2-thiazolyl] piperazine, M.P. of its dihydrochloride: 195°-200° C. (anhydrous ethanol).

(17) 1-[4-(4-phenylthiobenzyl)-2-thiazolyl] piperazine, M.P. of its hydrochloride: 165°-170° C. (anhydrous ethanol).

(18) 1-[4-(4-benzoylbenzyl)-2-thiazolyl] piperazine, M.P. of its dihydro chloride benihydrate: 230°-232° C. (methanol at 95%).

(19) 1-[4-(α-trifluoromethylbenzyl)-2-thiazolyl] piperazine, M.P.: 92°-95° C. (heptane).

(20) 1-[4-(α-methylbenzyl)-2-thiazolyl] piperazine, M.P. of its dihydrochloride: 212°-218° C. (ethanol).

(21) 1-(4-benzhydryl-2-thiazolyl) piperazine, M.P. of its dihydrochloride: 145°-148° C. (anhydrous ethanol).

(22) 1-(4-phenethyl-2-thiazolyl) piperazine, M.P. of its dihydrochloride hemihydrate: 220°-230° C. (ethanol).

(23) 1-[4-(4-fluorobenzyl)-2-thiazolyl] piperazine, M.P. of its hydrochloride: 187°-192° C. (anhydrous isopropanol)

(24) 1-[4-(2,4-dichlorobenzyl)-2-thiazolyl] piperazine.

(25) 1-[4-(3,4-dichlorobenzyl)-2-thiazolyl] piperazine.

(26) 1-[4-(α-methyl p. chlorobenzyl)-2-thiazolyl] piperazine.

(27) 1-[4-(4-p.chlorophenylthiobenzyl)-2-thiazolyl] piperazine.

(28) 1-[4-(4-p.chlorobenzoylbenzyl)-2-thiazolyl] piperazine.

The following examples illustrate the pharmaceutical compositions containing as active ingredient a compound of the general formula I.

EXAMPLE 29

| Formulation for one capsule containing 0.05 g of active ingredient: | | |
|---|---|---|
| 1-[4-(4-chlorobenzyl)-2-thiazoly] piperazine dihydrochloride | 0.05 | g |
| carboxymethyl starch | 0.005 | g |
| microcristalline cellulose | 0.080 8 | g |
| colloidal silica | 0.000 2 | g |
| magnesium stearate | 0.001 | g |
| talc | 0.003 | g |
| for one capsule n° 3 | | |

EXAMPLE 30

| Formulation for one coated tablet containing 0.100 g of active ingredient: | | |
|---|---|---|
| 1-[4-(4-phenylthiobenzyl)-2-thiazolyl] piperazine, hydrochloride | 0.100 | g |
| lactose | 0.085 | g |
| microcristalline cellulose | 0.050 2 | g |
| colloidal silica | 0.000 2 | g |
| polyvinylpyrrolidone | 0.010 | g |
| magnesium stearate | 0.0015 | g |
| talc | 0.005 | g |
| coating: | | |
| glycerol | 0.000 35 | g |
| hydroxypropylmethylcellulose | 0.006 35 | g |
| sodium laurylsulfate | 0.000 04 | g |
| titania | 0.001 9 | g |
| polyoxyethylene glycol 6 000 | 0.001 16 | g |
| magnesium stearate | 0.000 2 | g |

EXAMPLE 31

| Formulation for one capsule containing 0.100 g of active ingredient: | | |
|---|---|---|
| 1-[4-(4-benzoylbenzyl)-2-thiazolyl] piperazine, dihydrochloride | 0.100 | g |
| carboxymethyl starch | 0.005 | g |
| microcristalline cellulose | 0.087 8 | g |
| colloidal silica | 0.000 2 | g |
| magnesium stearate | 0.001 | g |
| talc | 0.006 | g |
| for one capsule n° 1 | | |

We claim:

1. A pharmaceutical composition, useful in the treatment of inflammation, containing as active ingredient an effective anti-inflammatory amount of a compound selected from the group consisting of:

a monosubstituted piperazine of the formula:

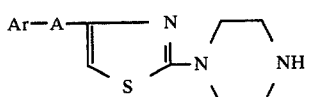

in which:

A is selected from the group consisting of $-(CH_2)_n-$ in which n is selected from 1, 2 and 3, and

in which R is selected from the group consisting of alkyl having 1 to 5 carbon atoms inclusive, trifluoromethyl, unsubstituted phenyl, and phenyl mono- and polysubstituted by a substituent selected from the group consisting of halogen, alkyl and alkoxy each having 1 to 5 carbon atoms inclusive, and trifluoromethyl, and Ar is selected from the group consisting of:
phenyl mono- and polysubstituted by a substituent selected from the group consisting of halogen, alkoxy having 1 to 5 carbon atoms inclusive, methylenedioxy, hydroxy, and trifluoromethyl, and unsubstituted phenyl when A is

R in such case being selected from trifluoromethyl, phenyl, halophenyl, lower-alkylphenyl, lower-alkoxyphenyl, and trifluoromethylphenyl, and physiologically-acceptable acid addition salts thereof, together with a pharmaceutically-acceptable carrier or diluent.

2. The pharmaceutical composition of claim 1 therein the active ingredient is present in an amount of 20 to 200 mg.

3. The composition of claim 1 wherein the active ingredient is selected from 1-[4-(3-chlorobenzyl)-2-thiazolyl] piperazine and its dihydrochloride and 1-[4-(4-chlorobenzyl)-2-thiazolyl] piperazine and its dihydrochloride.

4. A method of treating a living animal body afflicted with inflammation having an immunological component, comprising the step of administering an effective anti-inflammatory amount of a compound selected from the group consisting of:
a monosubstituted piperazine of the formula:

in which:
A is selected from the group consisting of —(CH$_2$)$_n$— in which n is selected from 1, 2 and 3, and

in which R is selected from the group consisting of alkyl having 1 to 5 carbon atoms inclusive, trifluoromethyl, unsubstituted phenyl, and phenyl mono- and polysubstituted by a substituent selected from the group consisting of halogen, alkyl and alkoxy each having 1 to 5 carbon atoms inclusive, and trifluoromethyl, and Ar is selected from the group consisting of:
phenyl mono- and polysubstituted by a substituent selected from the group consisting of halogen, alkoxy having 1 to 5 carbon atoms inclusive, methylenedioxy, hydroxy, and trifluoromethyl, and unsubstituted phenyl when A is

—CH—,
 |
 R

R in such case being selected from trifluoromethyl, phenyl, halophenyl, lower-alkylphenyl, lower-alkoxyphenyl, and trifluoromethylphenyl, and physiologically-acceptable acid addition salts thereof.

5. The method of claim 4 wherein the active ingredient is administered in an amount of 20 to 200 mg together with a pharmaceutically-acceptable carrier or diluent.

6. The method of claim 4 wherein the active ingredient is selected from 1-[4-(3-chlorobenzyl)-2-thiazolyl] piperazine and its dihydrochloride and 1-[4-(4-chlorobenzyl)-2-thiazolyl] piperazine and its dihydrochloride.

* * * * *